United States Patent [19]
Hauber

[11] Patent Number: 5,895,422
[45] Date of Patent: Apr. 20, 1999

[54] MIXED OPTICS INTRAOCULAR ACHROMATIC LENS

[76] Inventor: Frederick A. Hauber, 5347 Main St. Suite100, New Port Richey, Fla. 34652

[21] Appl. No.: 08/077,380

[22] Filed: Jun. 17, 1993

[51] Int. Cl.$^6$ .................................................. A61F 2/16
[52] U.S. Cl. ............................ 623/6; 351/161; 351/164; 351/166
[58] Field of Search .......................... 623/6; 351/161, 351/164, 166, 172

[56] References Cited

U.S. PATENT DOCUMENTS

| | | |
|---|---|---|
| 3,004,470 | 10/1961 | Ruhle . |
| 4,210,391 | 7/1980 | Cohen . |
| 4,338,005 | 7/1982 | Cohen . |
| 4,340,283 | 7/1982 | Cohen . |
| 4,550,973 | 11/1985 | Hufnagel . |
| 4,573,998 | 3/1986 | Mazzocco . |
| 4,641,934 | 2/1987 | Freeman . |
| 4,642,112 | 2/1987 | Freeman . |
| 4,676,792 | 6/1987 | Praeger . |
| 4,704,016 | 11/1987 | de Carle . |
| 4,731,078 | 3/1988 | Stoy et al. . |
| 4,846,552 | 7/1989 | Veldkamp et al. . |
| 4,881,804 | 11/1989 | Cohen . |
| 4,881,805 | 11/1989 | Cohen . |
| 4,995,714 | 2/1991 | Cohen . |
| 5,016,977 | 5/1991 | Baude et al. ................... 623/6 |
| 5,017,000 | 5/1991 | Cohen . |
| 5,053,171 | 10/1991 | Portney et al. . |
| 5,056,908 | 10/1991 | Cohen . |
| 5,076,684 | 12/1991 | Simpson et al. . |
| 5,116,111 | 5/1992 | Simpson et al. . |
| 5,117,306 | 5/1992 | Cohen ............................. 623/6 |
| 5,121,979 | 6/1992 | Cohen . |
| 5,121,980 | 6/1992 | Cohen . |
| 5,124,543 | 6/1992 | Kawashima . |
| 5,124,843 | 6/1992 | Leger et al. . |
| 5,152,787 | 10/1992 | Hamblen ........................ 623/6 |
| 5,152,788 | 10/1992 | Isaacson et al. ................ 623/6 |
| 5,153,772 | 10/1992 | Kathman et al. . |
| 5,201,762 | 4/1993 | Hauber ........................... 623/6 |
| 5,344,447 | 9/1994 | Swanson ......................... 623/6 |
| 5,384,604 | 1/1995 | Koch et al. ..................... 623/6 |

FOREIGN PATENT DOCUMENTS

86/03961  7/1986  WIPO .

OTHER PUBLICATIONS

Post, Jr., Charles T., MD, Comparison of Depth of Focus and Low–Contrast Acuities for Monofocal Versus Multifocal Intraocular Lens Patients at 1 Year, 99 Opthalmology, No. 11, at 1658–1664 (Nov. 1992).

Veldkamp et al., Binary Optics, Scientific American, at 92–97 (May 1992).

Koronkevich, Voldemar, Computer Synthesis of Diffraction Optical, at 277–313, Institute of Automation and Electrometry Siberian Branch of USSR Academy of Science Novoslblrsk, USSR (1989).

*Primary Examiner*—Paul B. Prebilic
*Attorney, Agent, or Firm*—James Creighton Wray; Meera P. Narasimhan

[57] ABSTRACT

Achromatic intraocular curved lenses have high order binary optic multiple level patterns for binary diffraction of light for correcting for chromatic aberration, making thin, lightweight, intraocular lenses that may be readily positioned in an eye, and that may bend and redirect light ray wavefronts to a retina for forming perceptible images with correct shapes and colors.

13 Claims, 5 Drawing Sheets

MIXED OPTICS INTRAOCULAR ACHROMATIC LENS

BACKGROUND OF THE INVENTION

Intraocular lenses of the type described herein are used primarily to treat problems of vision in a human eye.

A normal eye has two lenses with four refracting surfaces. Both lenses are convergent lenses which tend to focus light rays inward toward an axis of the eye. Greatest refraction takes place at the air-cornea interface, and lesser refraction occurs at the cornea-aqueous humour interface. Refraction again occurs at the aqueous humour-crystalline lens interface and again at the crystalline lens-vitreous humour interface. The aqueous humour and vitreous humour have approximately the same refractive index which is slightly below the refractive indices of the cornea and crystalline lens. The crystalline lens is composed of the capsule, the cortex and the nucleus, all of these surfaces having different indices of refraction allowing for color correction for chromatic aberrations due to refractions of incoming wavelengths of light.

When a crystalline lens is removed because of occlusion, for example with cataracts, its function may be replaced by a relatively thick converging lens worn outside of the eye. Preferably, in removing the crystalline lens the capsule is held intact to maintain separation between the vitreous humour and the aqueous humour.

In recent times, an intraocular lens is surgically positioned in the posterior chamber of the eye behind the iris and in front of the capsule. The intraocular lens, called a pseudophakos, is held in place with a haptic or other mount which extends outward from the lens and engages outer walls of the capsule or the sulcus. In another mounting method, the lens may be attached directly to the iris or to the chamber walls or within the cornea by any known means.

The pseudophakos has the advantage of eliminating the requirement for thick eyeglasses and increasing the field of vision, as compared with thick eyeglasses which may be used to replace a removed crystalline lens.

Techniques are known for anchoring lenses within the eye.

When a normal eye gazes upon an object, the cornea and crystalline lens focus an object upon a part of the retina which is in optical alignment with those lenses and which is called the macula, which joins the retina with the optic nerve and which is most sensitive to light.

A common problem which may develop, following cataract surgery, is the difficulty with correct color perception due to the inability of current lenses to correctly and concurrently refract the color wavelengths of light. An achromatic lens improves the color correction problem and thus improves overall image quality.

Current intraocular lenses are made of glass, plastics, silicone or hydrogel, polycarbonate or other suitable materials.

The use of a single element lens will allow for a focus of some wavelengths of light, but will cause a blur for other wavelengths. Some lenses produce false or distorted colors or color separation or fringing of images, known as chromatic aberration.

The construction of a conventional achromatic lenses is well known. Fine controlled forming, molding and grinding, matching spherical and non-spherical concave, convex or planar surfaces on lenses and joining exact opposite surfaces together with bonding material are known in the art.

Glass, such as combined lenses of flint and ground glass chosen for their different refractive indices, may be joined together as an achromatic lens, or plastics having different indices of refraction may be joined together or may be combined with glass of a desired index of refraction. One plastic well known for use in intraocular lenses is methyl methacrylate. Other suitable materials are known, such as polycarbonate, hydrogel, glass of silicone.

The inventor has created, and has a U.S. Pat. No. 5,201,762 for, an achromatic intraocular lens for use in the system made of two optical lens components joined together to form a doublet. The two lenses are preferably made of materials having different refractive indices. Refraction occurs at the interface as well as at the distal and proximal surface of the joined multiple lenses. Provided the appropriate degree of magnification or relocation of the image on the retina may be accomplished by the achromatic lens, that lens is a suitable multiple intraocular lens system.

One basic plastic may be used and impregnated with materials which provide differing indices of refraction in separate lens elements of the achromatic lens. The use of an achromatic lens consisting of two materials of different refractive indices allows for better color correction than lenses previously described.

The inventor continuously seeks to improve intraocular lenses. A need continues to exist for other chromatic aberration correcting intraocular lenses that may meet different requirements of patients.

SUMMARY OF THE INVENTION

The present invention describes the use and positioning of thin, lightweight color distortion-correcting binary achromatic lenses within the posterior or anterior chambers of the eye and describes the use of different forms of mixed binary and refractive chromatic aberration-avoiding intraocular achromatic lenses to treat different patient requirements.

The present invention provides intraocular mixed optics achromatic lenses. Mixed optics refer to refraction of a curved lens and diffraction of a binary lens. In one embodiment, the achromatic lens is positioned in a posterior chamber of an eye. In another form of the invention, the achromatic lens may be positioned in an anterior chamber of the eye. The new intraocular lens is positionable in a capsule. The lens may be positioned in a cornea or in a vitreous chamber of an eye.

High order multiple step diffractive patterns, which are referred to as high order binary optics, are preferred for the color correcting intraocular lenses of this invention. Multiple level binary patterns preferably are used in the intraocular achromatic lens. The patterns may be formed with lasers or may be formed by etching, as is standard in integrated circuit manufacture.

When etching is used, a quadruple etch is preferred, which produces sixteen levels or stair steps of diffraction and which produces a bright, clear lens with low light loss. A triple etch may be used which produces eight diffractive levels and still permits 90% or more light transmission. A double etch produces four levels of diffractive edges and is suitable.

Two intraocular mixed optics achromatic lenses may be constructed as a telescope in two portions having different or similar refractive indices. Both portions may be convergent. One portion may be convergent and the other portion may be divergent, or both portions may be divergent. Both lenses may have binary optics for color correction or a single lens may have chromatic correction with mixed optics.

The binary surface in the mixed optics lens may be on a flat surface or on the curved refractive surface, or embedded within the lens.

A divergent mixed optics achromatic lens may be used, for example, when a normal functional crystalline lens is present or when a pseudophakos has replaced an occluded crystalline lens, where is it difficult or unnecessary to remove the pseudophakos or the normal crystalline lens.

One form of the achromatic lens of the present invention uses a lens within a lens in which one lens body is embedded within another lens body, so that four sequentially aligned lens surfaces are employed. One or more surfaces may have binary optics. That form of the invention has many advantages, including the advantages of improved color correction, providing precise image and magnification control and providing different magnifications of the images in the center and peripheral areas of the compound achromatic lens within a lens.

The invention may be carried out using multiple lens within lens so that 2N-1 or other combinations of sequentially connected lens layers are encountered by light rays.

In one form of the invention, both the inner and outer lenses have convex outer surfaces. However, either or both surfaces of either or both lenses may be concave or planar.

The composition of the achromatic lens and the lens within lens of the present invention may be soft silicone or hydrogel or any foldable soft material or methyl methacrylate. The layers are of differing densities. The inside layer may be more dense than the outside layer. The reverse may be true. The multiple layers may have identical densities of differing materials which are basically different or which have been doped to change indices of refraction.

The entire lens within the lens system of the present invention may be made of a uniform material from surface to interior. The lenses may be formed of bendable plastics. The lenses may be capsules filled or fillable with fluid. The lenses may have liquid filled intermediate portions. In one form of the invention, the outer lens is a uniform material throughout which forms a cavity holding flowable material which forms the inner lens.

This invention is directed to reducing or eliminating chromatic aberration, color fringing and color shifting defects or other problems caused by refractive intraocular lenses. Conventional color defects in lenses are referred to generally as chromatic aberration.

One purpose of the intraocular mixed optics achromatic lens of the present invention is improved image quality by compensating for chromatic aberration.

Of primary interest in the present invention are intraocular chromatic aberration-correcting achromats made of mixed diffractive and refractive optics. The intraocular lenses are made as combined curved refractive lenses with diffractive lenses, more particularly binary lenses in which multiple level diffractive patterns are formed, machined or etched in at least one surface. The lenses are made as partially refractive lenses and partially diffractive high order binary lenses, i.e., as mixed lenses. Alternatively, the lenses may be partially flattened grooved refractive lenses and partially high order binary lenses. The refraction and diffraction are carefully balanced in the lenses, so that the partially binary and partially refractive lenses mutually correct chromatic aberrations in opposite directions to reunite colors of an image.

One achromatic intraocular lens has patterns for refraction and patterns for high order binary diffraction of light, making a thin, lightweight, bendable, form sustaining intraocular lens that may be readily positioned in an eye, and that may redirect light rays to a retina for forming perceptible images with correct color and with no discernible color fringes.

One intraocular achromatic lens is made of a plastic material and has first and second opposite light-transmitting surfaces for surgically positioning in optical alignment within an eye. One of the surfaces produces refraction of light rays. One of the surfaces has a high order binary pattern for bending light and focusing an image on a retina of the eye. The binary pattern may be on a surface of the lens, may be coated or may be formed within the lens.

The lens may be a mixed optics intraocular achromatic lens having two refractive lenses, with one or more refractive interfaces. The interface or an outer surface may contain high order binary multiple level diffractive patterns. The lenses are made of any suitable material. A haptic mount is connected to the lenses for mounting the achromatic lenses within an eye.

The plural intraocular lenses may have a first lens positioned entirely within a second lens.

A preferred intraocular lens has a high order binary lens pattern etched in the lens or on a surface for bending a wavefront and focusing an image without color distortions on a retina of an eye.

One embodiment has a second high order binary lens pattern on or in the achromatic intraocular lens for bending a wavefront and focusing an image on a retina. Another embodiment has a curved refraction pattern in the surface of the lens in combination with the binary multiple level etched diffractive pattern. One lens has a second diffraction surface on the lens.

A preferred intraocular achromatic lens is made of a plastic material and has on at least one of the surfaces a high order binary pattern for bending light and focusing an image on a retina of the eye.

Another preferred intraocular lens system has intraocular lenses made of soft foldable silicone or hydrogel or like material having a refractive surface and multiple level diffractive patterns for surgically positioning in optical alignment within an eye for concurrent image focusing and color correction. A haptic is connected to the achromatic lens for mounting the lens within a posterior or anterior chamber or a capsule of an eye.

By using the combination of refractive optics with high order binary optics, it is possible to eliminate chromatic aberration induced by using only a refractive element alone or a binary element alone. By forming high order binary optics in a refractive lens, the chromatic aberration can be eliminated.

Another preferred use of the mixed binary and refractive system is to combine a refractive lens with a binary lens to produce an intraocular telescopic device to project magnified images on large areas of the retina. Mixed optical lenses are also used in pairs to create an intraocular telescope that magnifies images and eliminates chromatic aberration.

These and further and other objects and features of the invention are apparent in the disclosure, which includes the above and ongoing written specification, with the claims and the drawings.

DETAILED DESCRIPTION OF THE DRAWINGS

Throughout the drawings, the lenses may be made of the preferred soft silicone, hydrogel or foldable soft material or standard methyl methacrylate.

Figure 1:
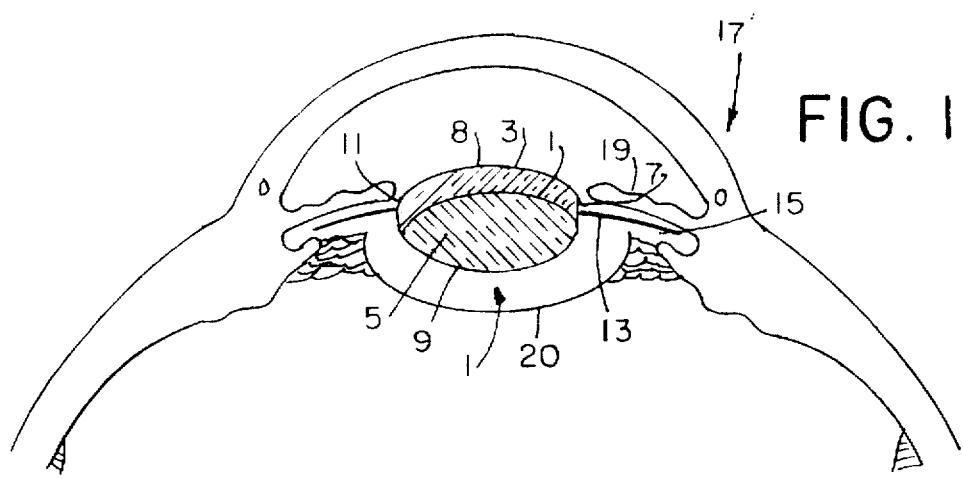
FIG. 1 is a schematic view of a frontal portion of an eye from which a crystalline lens has been removed and in which an achromatic lens has been placed in the posterior chamber.

FIG. 1 shows an achromatic lens 1 having a front lens portion 3 and a rear lens portion 5 joined together along a commonly shaped interface 7. Refraction occurs at the aqueous humour/front lens interface 8, at the lens interface 7 and at the aqueous humour/rear lens interface 9. In the embodiment shown in FIG. 1 both lenses are convergent lenses, lens 3 being slightly thicker at its center than at its outer edge 11, and the curvature of surface 3 being slightly greater than the curvature of interface 7.

A conventional haptic 13 extends outward to engage an outer surface of the posterior chamber 15 between the sulcus 16 and the iris 19.

Eye 17 has a cornea 18. The greatest refraction in the eye occurs at the cornea-air interface.

Capsule 20 is shown with a crystalline lens removed.

Figure 2:
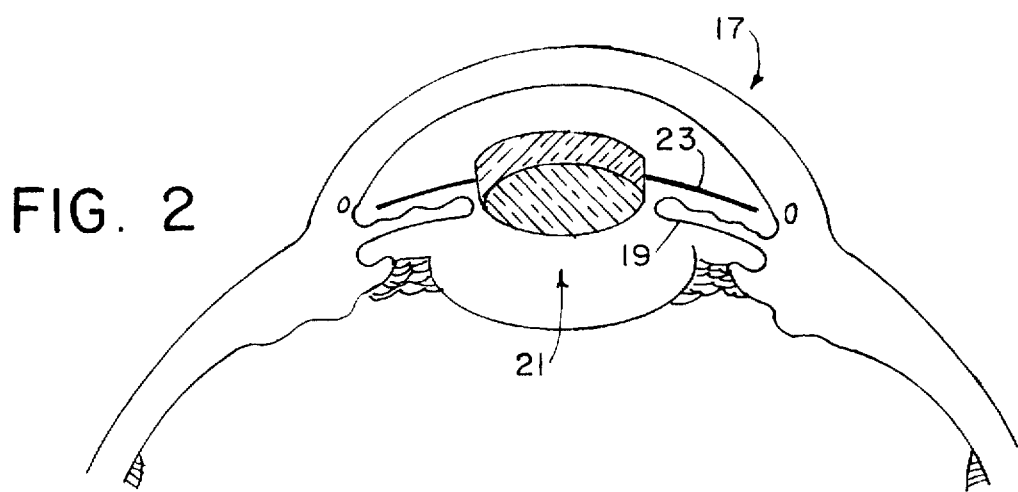
FIG. 2 is a similar view of an eye in which an achromatic lens has been replaced in an anterior chamber.

As shown in FIG. 2, achromatic lens 21 is positioned in the anterior chamber 22 of eye 17. Haptic 23 extends from the side of the achromatic lens to an outer wall of the anterior chamber just in front of the iris 19.

Binary multiple level diffractive patterns may be formed on either or both outer surfaces or within either or both lens or on an interface of the achromatic intraocular lenses in FIGS. 1–7.

Achromatic lens 21 has a similar configuration to the achromatic lens 1 shown in FIG. 2.

Figure 3:
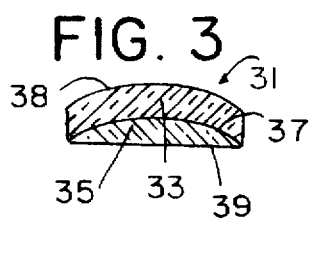
FIGS. 3, 4, 5 and 6 are details of differing forms of achromatic lenses.

In FIG. 3, an achromatic lens 31 is formed of two convergent lenses 33 and 35 having a common interface 37. Refraction occurs at the outer surface 38, the interface 37 and the planar rear face 39.

Figure 4:
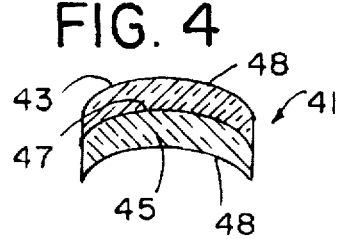

FIG. 4 shows an intraocular achromatic lens 41, in which both lenses 43 and 45 are convergent lenses and in which both lenses 43 and 45 are convex-concave lenses. In lens 41, the curvature of surface 48 is greater than the curvature of interface 47, and the curvature of surface 49 is less than the curvature of interface 47. A haptic may be mounted anywhere on the outer surface of the lens and may be mounted at the outer edge of the interface 47.

Figure 5:
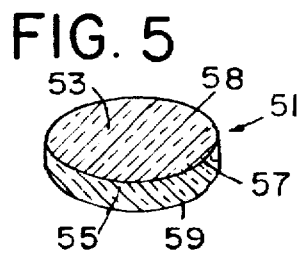

The intraocular achromatic lens 51 shown in FIG. 5 is similar to lens 1 shown in FIG. 1, with the exception that the convex-convex portion 53 is located in the front of the lens, and the concave-convex portion 55 is located at the rear of the lens. Refraction occurs at the outer surface 58 and 59, and at the interface 57. The lenses 53 and 55 are of different indices of refraction.

Figure 6:
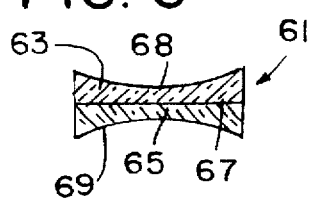

As shown in FIG. 6, a divergent intraocular achromatic lens has two divergent lens portions 63 and 65 joined at a planar interface 67. Refraction occurs at the concave surfaces 68 and 69 and at the interface 67. Lens 61 shown in FIG. 6 may be used in conjunction with an existing crystalline lens or pseudophakos. The haptic may be connected to one of the two lens portions 63 or 65, or may be connected at the outer edge of the interface 67.

Figure 7:
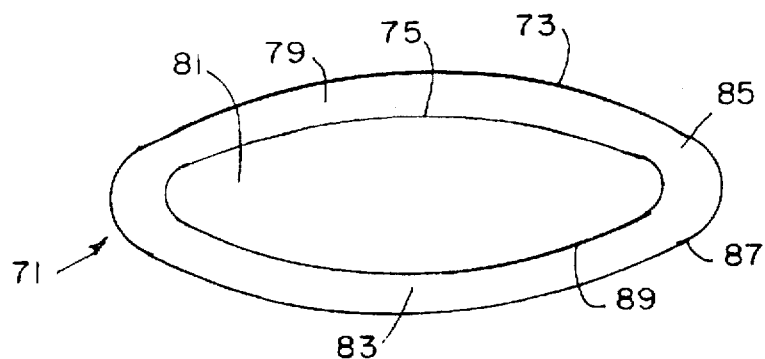
FIG. 7 shows a soft intraocular lens with two densities of silicone bonded together.

Referring to FIG. 7, a form of the invention, which is a lens within a lens, is generally indicated by the numeral 71. Lens 71 includes an outer lens body 73 and an inner body 75. Preferably both bodies are made of a soft, flexible plastic material, such as used in soft contact lenses. The center portion 77 of lens 71 provides three successive refracting layers 79, 81 and 83. The peripheral portions 85 of the lens 71 have one refractive portion with two refractor surfaces.

The lens 75 has a greater refractive index than the lens 73. Lens 75 is made of a more dense material than lens 73. In one embodiment, the lens sections 73 and 75 are made of a similar material having differing densities.

While the lenses have been shown for convenience in a relatively thick form, the lenses are thin; some are easily bendable and may be deformed and inserted through small incisions in a sclera of an eye and then expanded within an appropriate chamber in the eye. An inner lens may be supported within the outer lens by the restorable shape of the outer lens.

The lens within a lens and other achromatic lenses of the present invention may be formed as deflated capsules which are inserted in the eye. A lens is inflated with a liquid which is sealed in an impermeable covering. Alternatively, an intraocular lens may expand with the eye's own fluid which penetrates a permeable covering. The liquid may be a gel which takes the permanent predetermined shape of the outer surfaces 87 and 89 of the lens bodies.

In the example shown in FIG. 7, the central area of the achromatic lens within a lens tends to focus the light rays more sharply, while the outer portion, when devoid of the central lens, tends to bend the rays less and may be more suitable for close vision.

While the FIG. 7 lens within a lens is shown in an embodiment in which the outer lens substantially uniformly extends around the inner lens, peripheral areas 85 of the outer lens may be compressed so that the outer surface 87 of the outer lens closely approaches the outer surface 89 of the inner lens near the peripheral areas.

As shown in the drawings, shapes of the inner and outer lenses are similar. The inner or outer lens may have more or less curvature, having a greater or lesser radius of curvature than the other lens. That may be true for one or both surfaces of each lens.

While the lenses are shown as relatively thick, the lenses should be reduced to as small as practical an axial dimension. The refracting surfaces of the lenses are emphasized for purposes of illustration and the actual refracting surfaces may be different, depending on the requirements of individual eyes. The refraction may be arranged in an example of macular degeneration so that the projected image is enlarged to cover areas of the retina surrounding the macula.

The desired position of the lens is spaced from the iris in the posterior chamber or capsule. The lens may be mounted in the anterior chamber. Axial displacement of the intraocular achromatic lens from the iris allows the normal contraction and expansion which occurs with light variations to control pupillary size.

In some cases a capsule may have been destroyed, with attendant failure of separation between the vitreous and aqueous fluid cavities. In that case, the achromatic lens and the haptic may be designed to support the lens in a rearward position within the eye. Under that circumstance, it is preferable to mount the haptic in the posterior chamber, or to otherwise connect the haptic to the sulcus.

In all of the forms of the invention as shown in FIGS. 1–7, one or more or all of the outer faces and inner faces of the intraocular lens may be formed with etched or laser-formed multiple level patterns for high order binary optics diffraction by bending and redirecting wavefronts of light for forming chromatically correct images on the retina.

Figure 8:
FIG. 8 is a detail of a partially refractive and partially binary intraocular lens.

Referring to FIG. 8, an intraocular lens is schematically represented by the numeral 90. The lens has a curved refractive surface 91 and a high order binary multiple level diffractive pattern 93 in an opposite surface of the lens. Surface 91 may provide appropriate refraction for focusing an image, and pattern 93 may provide sufficient diffraction for color correction, or pattern 93 may provide additional diffraction for more precise focusing of the image.

Figure 9:
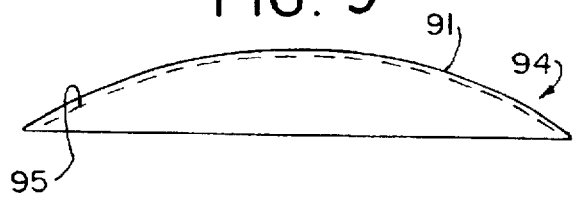
FIG. 9 is a schematic detail of another form of a partially refractive and partially binary intraocular lens.

FIG. 9 shows an intraocular lens 94 having a refractive surface 91 and a binary multiple level diffractive pattern 95 in a curved surface of the lens. The multiple level diffractive pattern 95 may be used independently or in conjunction with a pattern 93 to provide color correction and image positioning.

Figure 10:
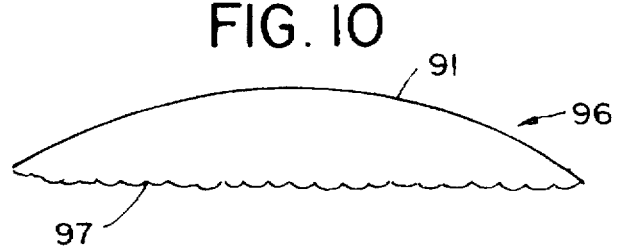
FIG. 10 is a schematic detail of a partially refractive and partially patterned diffractive intraocular lens.

FIG. 10 shows a lens 96 which has a refraction surface 91 and a diffraction surface 97.

Figure 11:
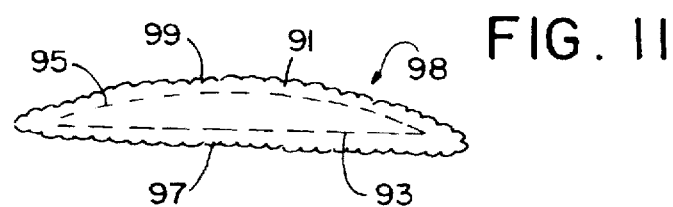
FIG. 11 is a view of a combined refractive and diffractive intraocular lens.

FIG. 11 is a schematic representation of a lens 98 which has a refractive surface 91 combined with a patterned diffractive surface 99 and a patterned binary diffractive surface 97, and additional binary diffractive focusing patterns 93 and 95 to produce a thin mixed optics intraocular lens with proper color correction in focused images.

Figure 12:
FIG. 12 is a side elevational schematic representation of a binary optics intraocular lens.

FIG. 12 is a schematic side elevational view of an intraocular lens 100 with an embedded or coated binary multiple level diffractive pattern 101.

Figure 13:
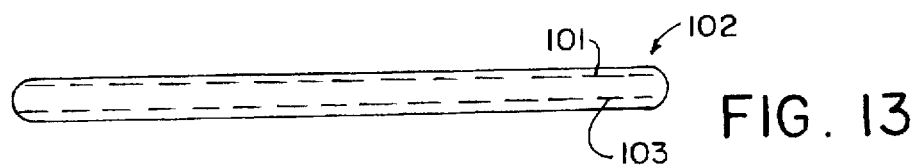
FIG. 13 is a schematic representation of an intraocular lens having two spaced binary multiple level diffractive patterns.

FIG. 13 schematically represents a side elevation of a lens 102 with binary multiple level diffractive patterns 101 and 103.

Figure 14:
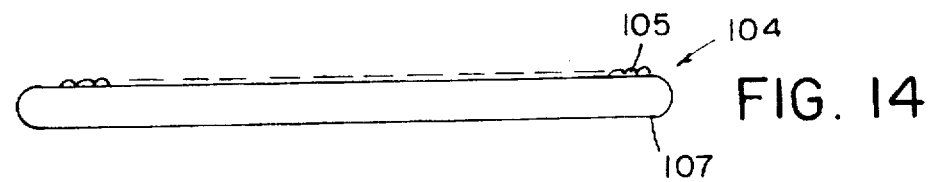
FIG. 14 is a schematic representation of a diffractive intraocular lens.

FIG. 14 schematically represents an intraocular lens 104 with a binary diffractive surface 105. A similar binary diffractive surface may be positioned on the opposite surface 107.

Figure 15:
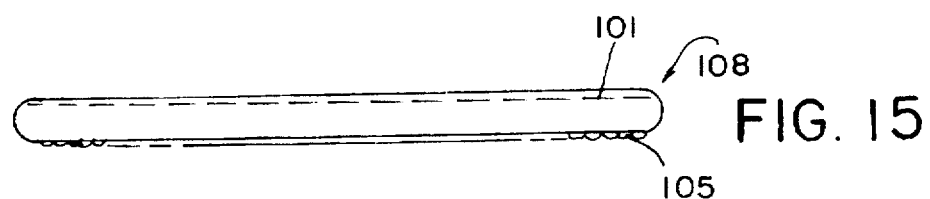
FIG. 15 is a schematic representation of a refractive and binary multiple level diffractive patterned intraocular lens.

FIG. 15 schematically shows an intraocular lens 108 with a binary pattern 101 embedded in one surface and a binary multiple level diffractive pattern 105 on the other surface. Lenses 100, 102, 104 and 108 provide correct color in focused images.

Figure 16:
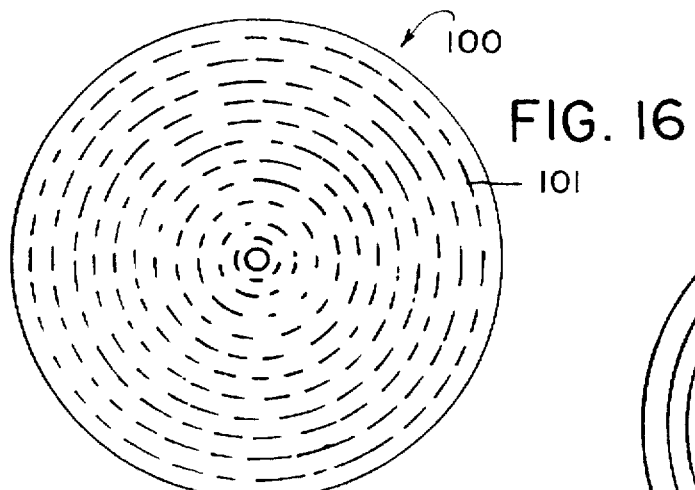
FIG. 16 is a schematic plan view of an interiorly patterned binary diffractive intraocular lens.

FIG. 16 is a schematic plan view of lens 100 with an embedded binary multiple level diffractive pattern 101. A schematic plan view of lens 102 is similar.

Figure 17:
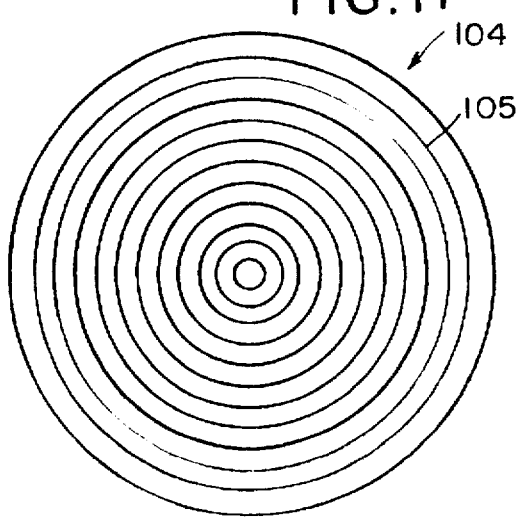
FIG. 17 is a schematic plan view of a surface patterned binary diffractive intraocular lens.

FIG. 17 is a schematic plan view of lens 104 shown in FIG. 14, with surface engraved binary multiple level diffractive patterns 105.

Figure 18:
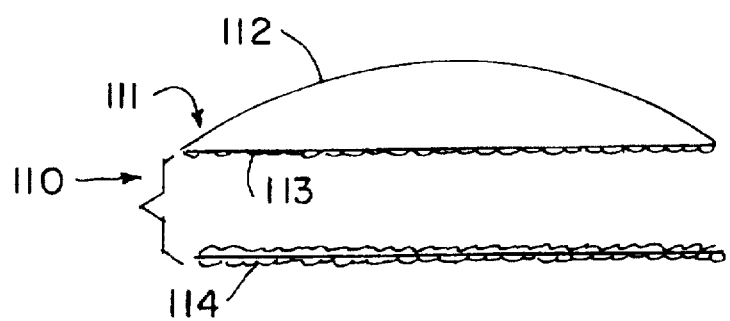
FIG. 18 is a schematic representation of an intraocular achromatic telescopic lens system with a mixed lens and a binary optics lens.

Referring to FIG. 18, telescopic system 110 comprises a mixed lens 111 with a refractive surface portion 112 and a binary diffractive surface 113, and a double binary diffractive lens 114 with engraved surfaces.

Figure 19:
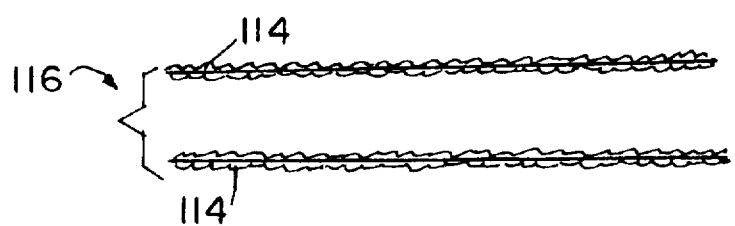
FIG. 19 is a schematic representation of a telescopic system with two binary optics lenses.

FIG. 19 shows a telescopic system 116 with two lenses 114 having binary diffractive surface patterns.

Figure 20:
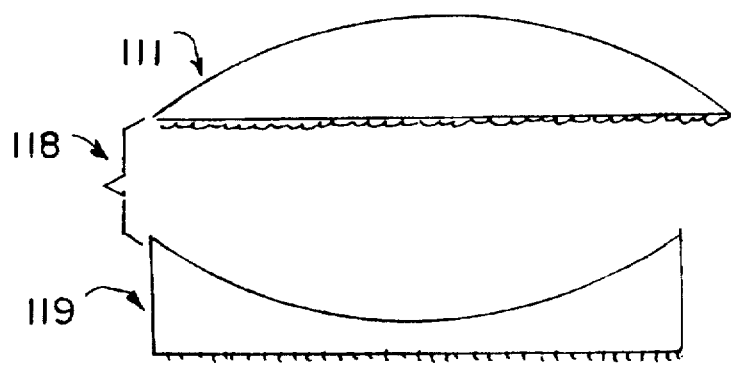
FIG. 20 is a schematic representation of a telescopic system with two mixed lenses.

FIG. 20 shows a telescopic system 118 with two mixed lenses 111 and 119, which include convex and concave refractive surfaces and binary diffractive surfaces.

Figure 21:
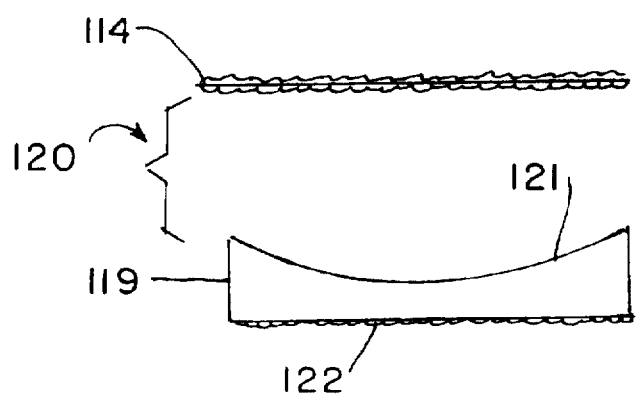
FIG. 21 is a schematic view of a telescope system with a binary optics lens and a mixed lens.

FIG. 21 shows a two lens telescope using a lens 114 with binary diffractive surfaces and a refractive and binary diffractive mixed lens 119 with a concave refractive surface 121 and a binary diffractive surface 122.

The higher order binary opticals can be used for a "multifocal" effect or a variable focal effect. The high order binary optic lenses can be used as corneal lenses (contact lenses) or intra lamellar implants in the cornea.

In all of the FIGS. 8–21, the binary diffraction portions are shown schematically enlarged. The patterns are etched, laser-formed or developed interior patterns.

Due to the thinness of the high order binary patterned diffractive surfaces in the mixed optics intraocular lenses, haptics can be modified by reducing strength and size.

Figure 22:
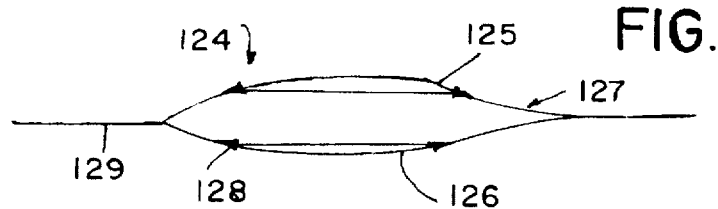
FIG. 22 schematically shows a telescope system made of two mixed lenses with a supporting haptic.
Figure 23:
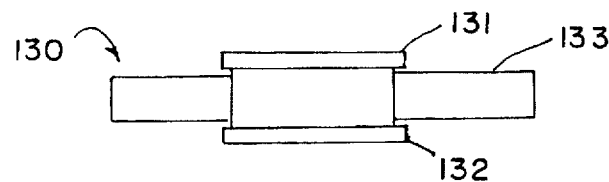
FIG. 23 schematically shows a telescope system with two mixed binary lenses and a supporting haptic.
Figure 24:
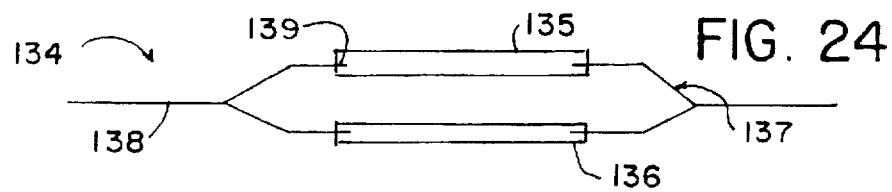
FIG. 24 schematically shows a telescopic lens system with thin binary optics lenses and a supporting haptic.

Examples of suitable haptics for use of lenses as telescopes are shown in FIGS. 22, 23 and 24.

FIG. 22 shows a telescope system 124 made of two mixed lenses 125 and 126, in which haptics 127 are made of small lens edge gripping portions 128 and larger surrounding portions 129. The surrounding portions may be "S" or "C" shaped or other peripheral modifications of the haptic to engage an interior surface of the eye.

FIG. 23 shows a telescope system 130 with two mixed lenses 131 and 132 held by a haptic 133 which extends outward from a fixed position between the lenses 131 and 132. The haptic may be bonded or physically fit to the lens. The haptic may be annular, or separate parts of a haptic may be mounted at opposite portions of the lens.

FIG. 24 shows a telescopic lens system 134 with thin mixed refractive and binary diffractive lenses 135 and 136 spaced apart by a haptic 137, which has an engaging part 138 for contacting an inner surface of an eye, and ends 139, which are embedded within openings in edges of the lenses. Haptic 137, as haptic 127, may be formed as a pair of oppositely extending plastic springs or plastic wires which are compatible with the eye inner surfaces and with the aqueous humour. The haptic may also be annular.

The distances between the two lenses may be modified to allow for greater or lesser magnification as required for the individual need.

Figure 25:
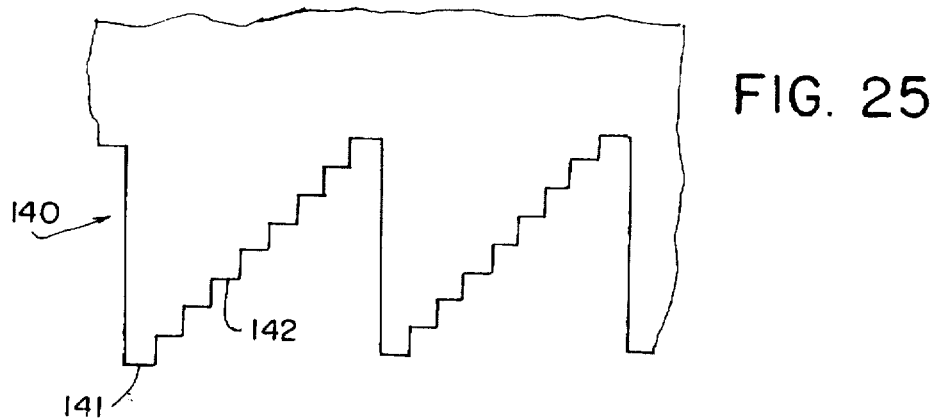
FIG. 25 is a schematic view of a high order binary optics diffraction pattern used in the present invention.

FIG. 25 shows a preferred high order binary optics multiple level refraction pattern 140 in a lens surface fragment 141 in which a stair step pattern 142 has been formed by triple etching or by laser on a single surface. In one example, each step is a fraction of a wavelength, and all steps total one wavelength. The pattern is regularly formed across the entire surface to bend a wavefront and correct for chromatic aberration.

Figure 26:
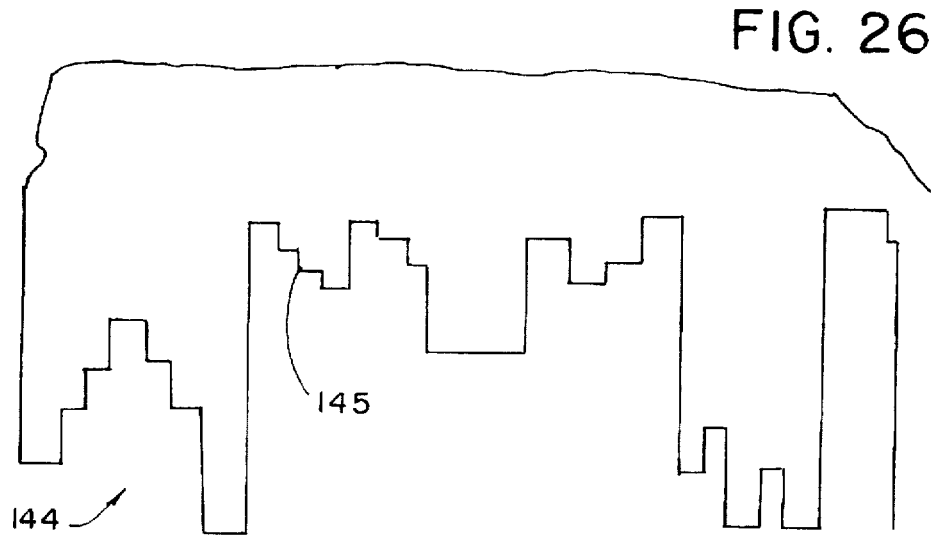
FIG. 26 schematically shows an irregularly formed higher order binary optics diffusion pattern.

FIG. 26 schematically shows an irregularly formed higher order binary optics multiple level diffusion pattern. The high order binary optics irregular pattern 144 is formed by etching or by laser on a single surface. Steps 145 diffract wavefronts by different amounts, resulting in correcting color or other defects or aberrations caused by lenses, or user to simulate other optical images.

While the invention has been described with reference to specific embodiments, modifications and variations of the invention may be constructed without departing from the scope of the invention, which is defined in the following claims.

I claim:

1. An intraocular achromatic lens apparatus, comprising an intraocular lens made of a synthesized plastic material and having first and second opposite outer light-transmitting intraocular surfaces for surgically positioning in optical alignment within an eye, and having on one of the surfaces a binary multiple level diffractive pattern to form one patterned surface for bending light, for correcting chromatic aberration and for focusing an image on a retina of the eye.

2. The apparatus of claim 1, wherein the intraocular lens further comprises two lenses, first and second outer surfaces and inner surfaces between the lenses, and a haptic mount connected to at least one of the lenses for mounting the achromatic lens within an eye, and wherein the binary multiple level diffractive pattern is associated with at least one of the surfaces.

3. The apparatus of claim 1, wherein the intraocular lens further comprises a first lens positioned entirely within a second lens, and further comprising two interface surfaces between the lenses in addition to the outer surfaces, and wherein the binary multiple level diffractive pattern is associated with at least one of the outer surfaces and interface surface.

4. The apparatus of claim 1, further comprising a binary multiple level diffractive pattern within the lens for bending a wavefront and focusing an image on a retina within the eye.

5. The apparatus of claim 4, wherein one of the surfaces comprises a curved refraction surface on the lens.

6. The apparatus of claim 5, further comprising a second curved refraction surface on the lens.

7. The apparatus of claim 1, further comprising a binary multiple level diffractive pattern on another surface of the lens.

8. An intraocular achromatic lens apparatus, comprising an intraocular lens having first and second opposite outer light-transmitting light-bending intraocular surfaces for surgically positioning in optical alignment within an eye, and having on one of the surfaces a binary diffractive pattern to form one patterned surface for bending light rays, correcting chromatic aberration and focusing an image on a retina of the eye.

9. The apparatus of claim 8, wherein the intraocular lens has two lenses, with interface surfaces between the lenses, and a haptic mount connected to at least one lens for mounting the achromatic intraocular lens within an eye, and wherein the binary diffractive pattern is associated with at least one of the group consisting of the opposite surfaces and interface surfaces.

10. The apparatus of claim 9, wherein the two intraocular lenses comprise a first lens positioned entirely within a second lens, and having two interface surfaces between the lenses in addition to the outer surfaces, which are on the second lens, and wherein the binary diffractive pattern is associated with at least one of the outer surfaces and interface surface.

11. The apparatus of claim 8, wherein the binary pattern is a multiple level diffractive pattern in the lens for bending a wavefront, correcting chromatic aberration and focusing an image on a retina.

12. The apparatus of claim 8, further comprising a curved refraction surface forming one of the surfaces of the intraocular lens.

13. The apparatus of claim 12, further comprising a second refraction surface forming another of the surfaces of the intraocular lens.

* * * * *